US011786213B2

(12) United States Patent
Hancock et al.

(10) Patent No.: US 11,786,213 B2
(45) Date of Patent: *Oct. 17, 2023

(54) SYSTEM AND METHOD FOR MULTIPATH PROCESSING OF IMAGE SIGNALS

(71) Applicant: PHILIPS IMAGE GUIDED THERAPY CORPORATION, San Diego, CA (US)

(72) Inventors: Andrew Hancock, Sacramento, CA (US); Jerome Mai, San Diego, CA (US); Joseph Hoffman, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,710

(22) Filed: Feb. 21, 2022

(65) Prior Publication Data
US 2022/0240890 A1 Aug. 4, 2022

Related U.S. Application Data

(63) Continuation of application No. 16/575,016, filed on Sep. 18, 2019, now Pat. No. 11,253,225, which is a (Continued)

(51) Int. Cl.
*A61B 8/12* (2006.01)
*A61B 8/00* (2006.01)
(Continued)

(52) U.S. Cl.
CPC ............... *A61B 8/12* (2013.01); *A61B 8/464* (2013.01); *A61B 8/467* (2013.01);
(Continued)

(58) Field of Classification Search
None
See application file for complete search history.

(56) References Cited

U.S. PATENT DOCUMENTS 3,301,258 A 1/1967 Werner
3,617,880 A 11/1971 Cormack et al.
(Continued)

FOREIGN PATENT DOCUMENTS

EP 1041373 10/2000
EP 01172637 1/2002
(Continued)

OTHER PUBLICATIONS

Ana et al. "Ringdown Reduction for an Intraluminal Ultrasound Array Using Depth Dependent Azimuthal Filters", 2002 IEEE Ultrasound Symposium, p. 177 (Year: 2002).*
(Continued)

*Primary Examiner* — Amelie R Davis
*Assistant Examiner* — Marjan Saboktakin

(57) ABSTRACT

The invention generally relates to intravascular imaging system and particularly to processing in multimodal systems. The invention provides an imaging system that splits incoming image data into two signals and performs the same processing step on each of the split signals. The system can then send the two signals down two processing pathways. Methods include receiving an analog image signal, transmitting the received signal to a processing system, splitting the signal to produce a first image signal and a second image signal, and performing a processing operation on the first image signal and the second image signal. The first and second signal include substantially the same information as one another.

22 Claims, 8 Drawing Sheets

Related U.S. Application Data continuation of application No. 14/106,260, filed on Dec. 13, 2013, now Pat. No. 10,420,530.

(60) Provisional application No. 61/745,388, filed on Dec. 21, 2012.

(51) Int. Cl.
  *G01S 7/52* (2006.01)
  *G01S 15/89* (2006.01)

(52) U.S. Cl.
  CPC ............ *G01S 7/52082* (2013.01); *A61B 8/56* (2013.01); *G01S 7/52053* (2013.01); *G01S 7/52084* (2013.01); *G01S 15/8956* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,315,999 A * | 5/1994 | Kinicki ............... G01S 7/52073 600/443 |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |

(56) References Cited

U.S. PATENT DOCUMENTS

| | | |
|---|---|---|
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,142,942 A * | 11/2000 | Clark ............... G01S 7/52025 600/443 |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |

(56) References Cited

U.S. PATENT DOCUMENTS

| | | |
|---|---|---|
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |

(56) References Cited

U.S. PATENT DOCUMENTS

| | | |
|---|---|---|
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |

(56) References Cited

U.S. PATENT DOCUMENTS

| | | |
|---|---|---|
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0201572 A1* | 9/2005 | Lindahl .............. H03G 5/165 381/103 |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0009695 A1 | 1/2006 | Mathew |
| 2006/0013523 A1 | 1/2006 | Chiidlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |

(56) References Cited

U.S. PATENT DOCUMENTS

| | | |
|---|---|---|
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | Mceowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0142781 A1 | 6/2010 | Walker |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0174190 A1* | 7/2010 | Hancock ............ G01S 7/52033 600/443 |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1* | 4/2011 | Moore ................ G01S 7/52071 600/447 |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |

(56) References Cited

U.S. PATENT DOCUMENTS

| | | |
|---|---|---|
| 2011/0319762 A1* | 12/2011 | Lerman .................. A61B 8/12 600/443 |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 | 4/2012 |
| GB | 2280261 | 1/1995 |
| JP | H04236949 A | 8/1992 |
| JP | H06249833 A | 9/1994 |
| JP | 2000-262461 | 9/2000 |
| JP | 2000-292260 | 10/2000 |
| JP | 2001-125009 | 5/2001 |
| JP | 2001-272331 | 10/2001 |
| JP | 2002-374034 | 12/2002 |
| JP | 2003-143783 | 5/2003 |
| JP | 2003-172690 | 6/2003 |
| JP | 2003-256876 | 9/2003 |
| JP | 2003-287534 | 10/2003 |
| JP | 2005-274380 | 10/2005 |
| JP | 2006-184284 | 7/2006 |
| JP | 2006-266797 | 10/2006 |
| JP | 2006-313158 | 11/2006 |
| JP | 2007-024677 | 2/2007 |
| JP | 2009-233001 | 10/2009 |
| JP | 2011-56786 | 3/2011 |
| WO | 91/01156 | 2/1991 |
| WO | 92/16865 | 10/1992 |
| WO | 93/06213 | 4/1993 |
| WO | 93/08829 | 5/1993 |
| WO | 98/38907 | 9/1998 |
| WO | 98/57583 | 12/1998 |
| WO | 00/11511 | 3/2000 |
| WO | 00/044296 | 8/2000 |
| WO | 01/11409 | 2/2001 |
| WO | 03/062802 | 7/2003 |
| WO | 03/073950 | 9/2003 |
| WO | 2004/010856 | 2/2004 |
| WO | 2004/023992 | 3/2004 |
| WO | 2004/096049 | 11/2004 |
| WO | 2005/047813 | 5/2005 |
| WO | 2005/106695 | 11/2005 |
| WO | 2006/029634 | 3/2006 |
| WO | 2006/037132 | 4/2006 |
| WO | 2006/039091 | 4/2006 |
| WO | 2006/061829 | 6/2006 |
| WO | 2006/068875 | 6/2006 |
| WO | 2006/111704 | 10/2006 |
| WO | 2006/119416 | 11/2006 |
| WO | 2006/121851 | 11/2006 |
| WO | 2006/130802 | 12/2006 |
| WO | 2007/002685 | 1/2007 |
| WO | 2007/025230 | 3/2007 |

(56) References Cited

FOREIGN PATENT DOCUMENTS

| WO | 2007/045690 | 4/2007 |
| --- | --- | --- |
| WO | 2007/058895 | 5/2007 |
| WO | 2007/067323 | 6/2007 |
| WO | 2007/084995 | 7/2007 |
| WO | 2008/058084 | 5/2008 |
| WO | 2008/069991 | 6/2008 |
| WO | 2008/107905 | 9/2008 |
| WO | 2009/009799 | 1/2009 |
| WO | 2009/009801 | 1/2009 |
| WO | 2009/046431 | 4/2009 |
| WO | 2009/121067 | 10/2009 |
| WO | 2009/137704 | 11/2009 |
| WO | 2011/06886 | 1/2011 |
| WO | 2011/038048 | 3/2011 |
| WO | 2011/081688 | 7/2011 |
| WO | 2012/003369 | 1/2012 |
| WO | 2012/061935 | 5/2012 |
| WO | 2012/071388 | 5/2012 |
| WO | 2012/087818 | 6/2012 |
| WO | 2012/098194 | 7/2012 |
| WO | 2012/109676 | 8/2012 |
| WO | 2012/130289 | 10/2012 |
| WO | 2012/154767 | 11/2012 |
| WO | 2012/155040 | 11/2012 |
| WO | 2013/033414 | 3/2013 |
| WO | 2013/033415 | 3/2013 |
| WO | 2013/033418 | 3/2013 |
| WO | 2013/033489 | 3/2013 |
| WO | 2013/033490 | 3/2013 |
| WO | 2013/033592 | 3/2013 |
| WO | 2013/126390 | 8/2013 |
| WO | 2014/109879 | 7/2014 |

OTHER PUBLICATIONS

Carotenuto et al. "Spatial resolution enhancement of ultrasound images using neural networks", IEEE, 2002, pp. 1039-1049 (Year: 2002).*
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1 ):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8): 1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.

(56) References Cited

OTHER PUBLICATIONS

Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3x3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelsor interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning: Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells EMBO J., 10:3655-3659.
Trolier-McKinstry et al., 2004, Thin Film Piezoelectric for MEMS, Journal of Eleclroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).

(56) References Cited

OTHER PUBLICATIONS

International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19): 1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinica Cardiology, 14(11):868-874.
Abdi et al., 2010, Principal component analysis, Wiley Interdisciplinary Reviews: Computational Statistics 2:433-459.

(56) References Cited

OTHER PUBLICATIONS

Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2): 179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329): 1078-1080.
Ergun et al., 2003, Capacitive Micromachined Ultrasonic Transducers: Theory and Technology, Journal of Aerospace Engineering, 16(2)76-84.
Evans et al., 2006, Optical coherence tomography to identify intramucosa carcinoma and high-grade dysplasia in Barrett's esophagus, Clin Gast Hepat4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, Qut.
Forslner& Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
International Search Report and Written Opinion dated Apr. 9, 2014, for international application No. PCT/US13/75089, filed Dec. 13, 2013 (8 pages).
Ana et al "Ringdown Reduction for an Intraluminal Ultrasound Array using Depth Dependent Azimuthal Filters", IEEE Ultrasound Symposium, 2002.
Paula Zitko Bernandino Alves et al "Comparison of Techniques for Speckle Noise Reduction in Breast Ultrasound Images", IFMBE Proceedings, vol. 25/11, pp. 569-571. 2009.

(56) References Cited

OTHER PUBLICATIONS

Carotenute et al. "Spatial Resolution Enhancement of Ultrasound Images using Neural Networks", IEEE, 2002.

* cited by examiner

SYSTEM AND METHOD FOR MULTIPATH PROCESSING OF IMAGE SIGNALS

CROSS-REFERENCE TO RELATED APPLICATIONS

This application is a continuation of U.S. application Ser. No. 16/575,016, filed Sep. 18, 2019, now U.S. Pat. No. 11,253,225, which is a continuation of U.S. application Ser. No. 14/106,260, filed Dec. 13, 2013, now U.S. Pat. No. 10,420,530, which claims the benefit of, and priority to, U.S. Provisional Application Ser. No. 61/745,388, filed Dec. 21, 2012, the entireties of which are incorporated by reference herein.

FIELD OF THE INVENTION

The invention generally relates to intravascular imaging system and particularly to processing in multimodal systems.

BACKGROUND

Ultrasound imaging is used in medicine to examine tissue with sound signals at a frequency higher than the normal range of human hearing. To illustrate, engine noise from a typical truck might include 125 Hz sounds while birds may chirp at about 6,000 Hz. A typical intravascular ultrasound device might operate at 40,000,000 Hz (i.e., 40 MHz).

In medical ultrasound, a probe device sends sound waves through tissue. The sound waves bounce off features in the tissue and back to the transducer. The transducer converts the waves to an electrical signal and sends it to an image processing system. Typically, the image processing system converts the electrical signal to a digital signal, which can then be displayed on a computer monitor (allowing a doctor to see the patient's blood vessels) or stored for other analyses.

In fact, looking at the tissue is but one use of IVUS. Some IVUS systems are used to perform "virtual histology", which involves analyzing an ultrasound signal to classify features in a patient's tissue (e.g., plaque, dead tissue, healthy tissue). IVUS can also be used to study the flow of blood within a patient. The velocity at which blood is flowing will typically produce a characteristic Doppler signature. This information can help identify is a patient is suffering from restricted blood flow due to, for example, atherosclerosis, or plaques.

The very fact that an IVUS signal may be put to more than one use is associated with challenges in the design and maintenance of IVUS systems. Any change in the signal processing that benefits one intended use can cause problems in another end-use. For example, in some ultrasound systems, transient resonances from the transducer produce signals, called ringdown, that detract from a visual display. A processing step can be added to the system that removes the ringdown from the signal. However, the ringdown signal does provide some data about the tissue that is useful in virtual histology. Thus, if the system is also used for virtual histology, yet another step must be added that puts the ringdown data back into the signal for the virtual histology application.

U.S. Patent Publication 2011/0087104 to Moore describes a system that "splits" the signal for imaging and for parametric (e.g., virtual histology) analysis. However, such a system requires duplicate, parallel hardware components that operate in tandem in the different signal processing pathways. Not only does duplicate internal hardware require additional design and manufacturing costs, it also raises some significant difficulties in subsequent modifications of the systems to add other image analysis tools.

SUMMARY

The invention provides an imaging system that splits incoming image data into two signals and performs the same processing step on each of the split signals.

The system can then send the two signals down two processing pathways. Where one of the pathways is used to provide medical information, a subsequent change or addition to the other pathway does not affect the first pathway. For example, if one pathway provides a grayscale image and the other is used in virtual histology, the addition of a processing step such as ringdown subtraction in the grayscale pathway requires neither a compensating step in the virtual histology pathway nor additional hardware to be added. The system is flexible because future changes, included unforeseen changes, can be accommodated without complex measures. The flexibility of the system lowers lifetime operating costs of medical imaging operations due to the fact that new modalities can be implemented without new processing hardware or engineering efforts. Lower operating costs allows use of the medical imaging system to reach a greater number of patients, improving a greater number of lives.

In certain aspects, the invention provides a method of imaging tissue that includes receiving an analog image signal from an ultrasonic transducer, transmitting the received signal to a processing system, splitting the signal to produce a first image signal and a second image signal, and performing a processing operation on the first image signal and the second image signal. The first and second signal include substantially the same information as one another. For example, an image signal can be split and then each copy can be amplified as a method of time gain compensation. The two TGC amplified signals can then be digitized in parallel. Alternatively, the analog signal can be digitized prior to (e.g., just prior to) splitting. The processing that is performed on both signals can be performed within the same processor. For example, a field-programmable gate array can be deployed with a redundant logic that does the same thing in parallel to each signal. Alternatively or additionally, the processor could include an application specific integrated circuit, a general purpose microprocessor, or other hardware. A signal can also be processed by hardware such as an amplifier or filter. In some embodiments, methods of the invention include deriving different types of images or signals (e.g., 2D displays and virtual histology analyses) from the first and second signal, i.e., the first type of image comprises a grayscale image and the second type of signal comprises a tissue characterization.

In related aspects, the invention provides an intravascular ultrasound imaging system that includes an elongated catheter with a transducer at a distal portion of the catheter and coupled to processing system at a proximal portion of the catheter. The system is operable to receive an analog image signal from the transducer; split the signal into a first image signal and a second image signal—the first image signal comprising substantially all of the information of the second image signal—and perform a processing operation on the first image signal and the second image signal. The system may further include one or more of a time gain compensation amplifier operable to produce a TGC amplified first signal and a TGC amplified first signal; an analog-digitalconverter; a field-programmable gate array configured to perform the processing operation; an application-specific integrated processor, a low-band pass filter; and a massively parallel processor array.

DETAILED DESCRIPTION

The invention provides an imaging system that splits incoming image data into two signals and performs the same processing step on each of the split signals.

Figure 1:
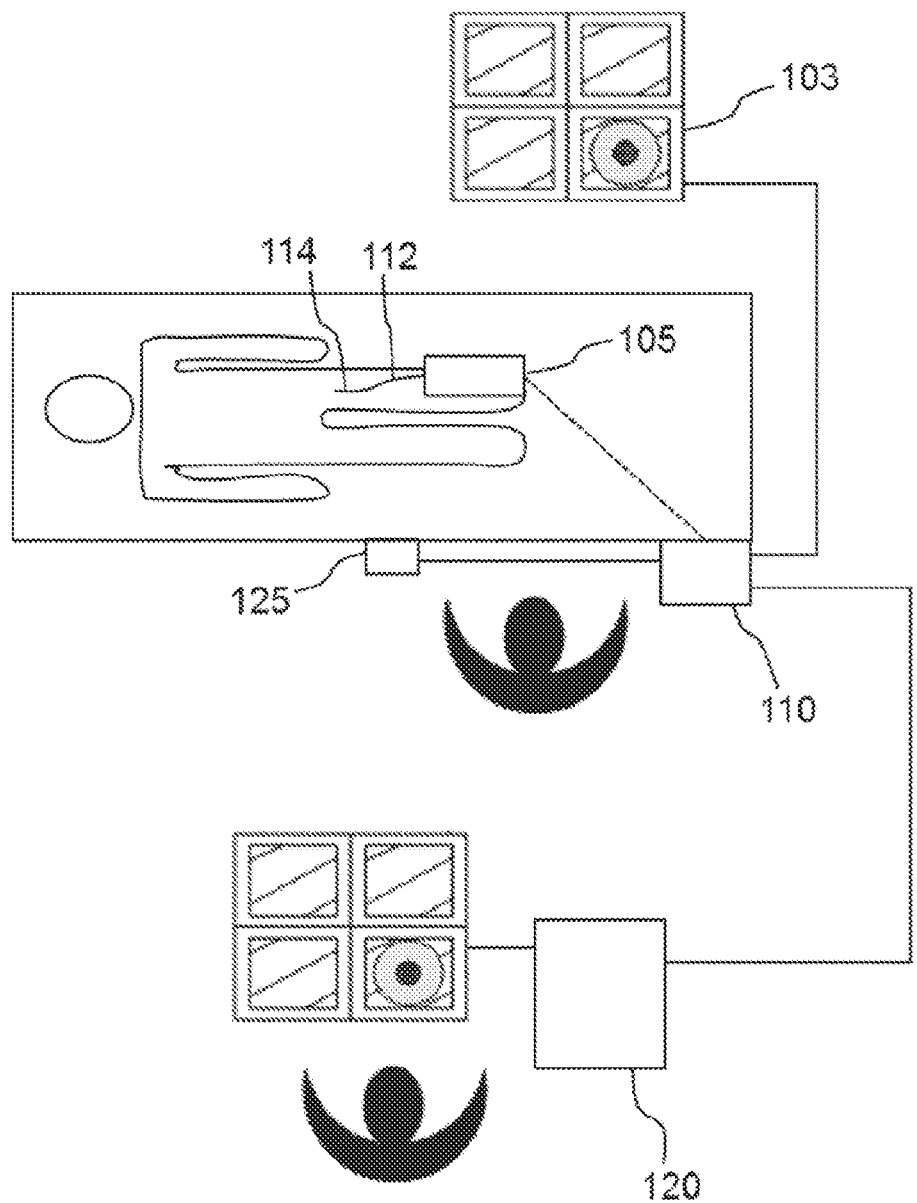
FIG. 1 shows an IVUS system according to certain embodiments of the invention.

FIG. 1 shows a diagram of an exemplary IVUS system 101 according to certain embodiments of the invention. An operator uses control station 110 and optional navigational device 125 to operate catheter 112 via patient interface module (PIM) 105. At a distal tip of catheter 112 is an ultrasonic transducer 114. Computer device 120 works with PIM 105 to coordinate imaging operations. Imaging operations proceed by rotating an imaging mechanism via catheter 112 while transmitting a series of electrical impulses to transducer 114 which results in sonic impulses being sent into the patient's tissue. Backscatter from the ultrasonic impulses is received by transducer 114 and interpreted to provide an image on monitor 103. System 101 is operable for use during diagnostic ultrasound imaging of the peripheral and coronary vasculature of the patient. System 101 can be configured to automatically visualize boundary features, perform spectral analysis of vascular features, provide qualitative or quantitate blood flow data, or a combination thereof. Systems for IVUS suitable for use with the invention are discussed in U.S. Pat. No. 6,673,015; U.S. Pub. 2012/0265077; and U.S. RE40,608 E, the contents of which are incorporated by reference in their entirety for all purposes.

Operation of system 101 employs a sterile, single use intravascular ultrasound imaging catheter 112. Catheter 112 is inserted into the coronary arteries and vessels of the peripheral vasculature under angiographic guidance. Catheters are described in U.S. Pat. Nos. 7,846,101; 5,771,895; 5,651,366; 5,176,141; U.S. Pub. 2012/0271170; U.S. Pub. 2012/0232400; U.S. Pub. 2012/0095340; U.S. Pub. 2009/0043191; U.S. Pub. 2004/0015065, the contents of which are incorporated by reference herein in their entirety for all purposes. System 101 may be integrated into existing and newly installed catheter laboratories (i.e., "cath labs" or "angiography suites"). The system configuration is flexible in order to fit into the existing catheter laboratory work flow and environment. For example, the system can include industry standard input/output interfaces for hardware such as navigation device 125, which can be a bedside mounted joystick. System 101 can include interfaces for one or more of an EKG system, exam room monitor, bedside rail mounted monitor, ceiling mounted exam room monitor, and server room computer hardware.

System 101 connects to the IVUS catheter 112 via PIM 105, which may contain a type CF (intended for direct cardiac application) defibrillator proof isolation boundary. All other input/output interfaces within the patient environment may utilize both primary and secondary protective earth connections to limit enclosure leakage currents. The primary protective earth connection for controller 125 and control station 110 can be provided through the bedside rail mount. A secondary connection may be via a safety ground wire directly to the bedside protective earth system. Monitor 103 and an EKG interface can utilize the existing protective earth connections of the monitor and EKG system and a secondary protective earth connection from the bedside protective earth bus to the main chassis potential equalization post. Monitor 103 may be, for example, a standard SXGA (1280×1024) exam room monitor. System 101 includes computer device 120 to coordinate operations.

Computer device 120 generally includes one or more processor coupled to a memory. Any suitable processor can be included such as, for example, a general-purpose microprocessor, an application-specific integrated circuit, a massively parallel processing array, a field-programmable gate array, others, or a combination thereof. In some embodiments, computer 120 can include a high performance dual Xeon based system using an operating system such as Windows XP professional. Computer 120 may be provided as a single device (e.g., a desktop, laptop, or rack-mounted unit, or computer 120 may include different machines coupled together (e.g., a Beowulf cluster, a network of servers, a server operating with a local client terminal, other arrangements, or a combination thereof).

Computer device 120 may be configured to perform processing on more than one image modality (e.g., in parallel). For example, computer 120 may operate with real time intravascular ultrasound imaging while simultaneously running a tissue classification algorithm referred to as virtual histology (VH). The application software can include a DICOM3 compliant interface, a work list client interface, interfaces for connection to angiographic systems, or a combination thereof. Computer device 120 may be located in a separate control room, the exam room, or in an equipment room and may be coupled to one or more of a custom control station, a second control station, a joystick controller, a PS2 keyboard with touchpad, a mouse, or any other computer control device.

Computer device 120 may generally include one or more USB or similar interfaces for connecting peripheral equipment. Available USB devices for connection include the custom control stations, optional joystick 125, and a color printer. In some embodiments, computer 120 includes one or more of a USB 2.0 high speed interface, a 10/100/1000 baseT Ethernet network interface, AC power jack, PS2 jack, Potential Equalization Post, 1 GigE Ethernet interface, microphone and line jacks, VGA video, DVI video interface, PIM interface, ECG interface, other connections, or a combination thereof. As shown in FIG. 1, computer device 120 is generally linked to control station 110.

Figure 2:
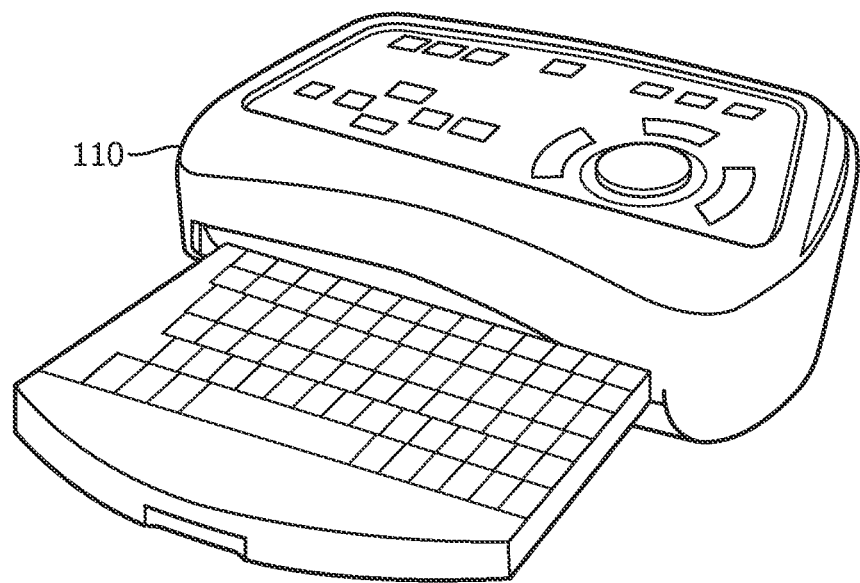
FIG. 2 shows a control station for an imaging system.

FIG. 2 shows a control system 110 according to certain embodiments. Control station 110 may be provided by any suitable device, such as a computer terminal (e.g., on a kiosk). In some embodiments, control system 110 is a purpose built device with a custom form factor. A slide out keyboard is located on the bottom for manual text entry. Control station 110 may be designed for different installations options. The station can be placed directly on a desktop surface. With the optional bedside mounting kit, control station 110 can be affixed directly to the bedside rail. This mounting kit is slipped over the rail and fixed in place by tightening two hand screws. Control station 110 can include a standard four hole VESA mount on the underside to allow other mounting configurations. Control system 110 may provide a simple-to-use interface with frequently-operated functions mapped to unique switches. Control station 110 may be powered from, and may communicate with, computer 120 using a standard USB 1.1 interface. The system may include a control panel 115. In some embodiments, multiple control panels 115 are mounted in both the exam room and/or the control room. A control station for use with the invention is discussed in U.S. Pat. No. 8,289,284, the contents of which are incorporated by reference in their entirety for all purposes.

Figure 3:
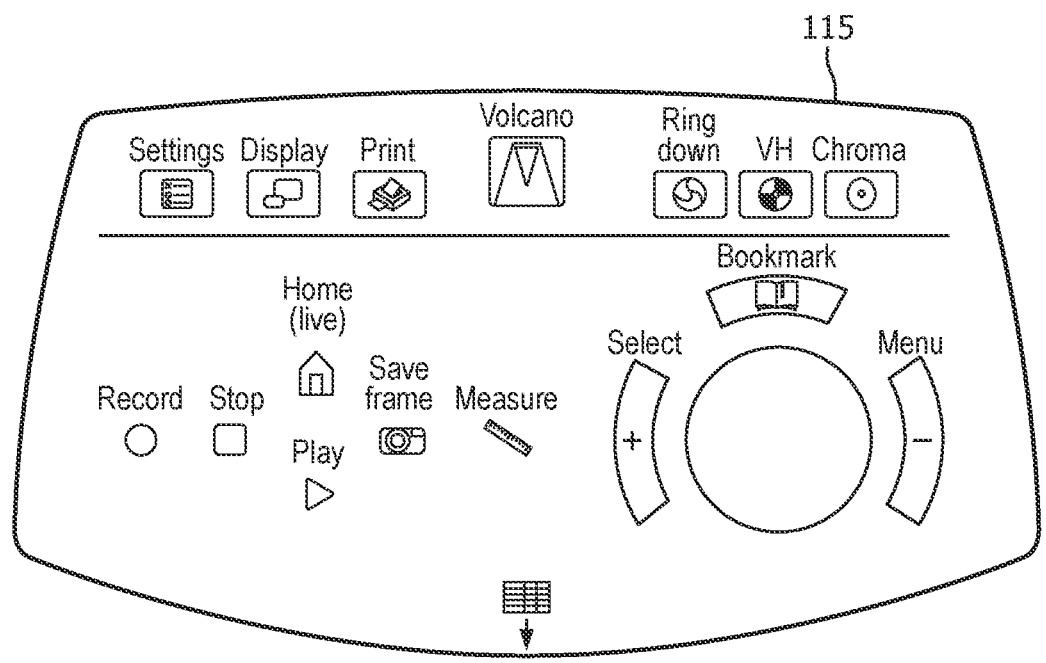
FIG. 3 shows an control panel of a control station of an imaging system.

FIG. 3 shows an control panel 115 of control system 110 according to certain embodiments. Frequently-operated functions are mapped to contact closure switches. Those dome switches are covered with a membrane overlay. The use of dome switches provides a tactile feedback to the operator upon closure. Control panel 115 may include a pointing device such as a trackball to navigate a pointer on the graphical user interface of the system.

Control panel 115 may include several screen selection keys. The settings key is used to change system settings like date and time and also permits setting and editing default configurations. The display key may be used to provide enlarged view for printing. In some embodiments, the print key prints a 6×4 inch photo of the current image on the screen. Control panel 115 may include a ringdown key that toggles the operation of ringdown subtraction. A chroma key can turn blood flow operations on and off. The VH key can operate the virtual histology engine. A record, stop, play, and save frame key are included for video operation. Typically, the home key will operate to display the live image. A menu key provides access to measurement options such as diameter, length, and borders. Bookmark can be used while recording a loop to select specific areas of interest. Select (+) and Menu (−) keys are used to make selections.

In some embodiments, the system includes a joystick for navigational device 125. The joystick may be a sealed off-the-shelf USB pointing device used to move the cursor on the graphical user interface from the bedside. System 101 may include a control room monitor, e.g., an off-the-shelf 19" flat panel monitor with a native pixel resolution of 1280×1024 to accept DVI-D, DVI-I and VGA video inputs.

Control station 110 is operably coupled to PIM 115, from which catheter 112 extends. Catheter 112 includes an ultrasound transducer 114 located at the tip. Any suitable IVUS transducer may be used. For example, in some embodiments, transducer 114 is driven as a synthetic aperture imaging element. Imaging transducer 114 may be approximately 1 mm in diameter and 2.5 mm in length. In certain embodiments, transducer 114 includes a piezoelectric component such as, for example, lead zirconium nitrate or PZT ceramic. The transducer may be provided as an array of elements (e.g., 64), for example, bonded to a Kapton flexible circuit board providing one or more integrated circuits. This printed circuit assembly may rolled around a central metal tube, back filled with an acoustic backing material and bonded to the tip of catheter 114. In some embodiments, signals are passed to the system via a plurality of wires (e.g., 7) that run the full length of catheter 112. The wires are bonded to the transducer flex circuit at one end and to a mating connector in PIM 105 at the other. The PIM connector may also contains a configuration EPROM. The EPROM may contain the catheter's model and serial numbers and the calibration coefficients which are used by the system. The PIM 105 provides the patient electrical isolation, the beam steering, and the RF amplification. PIM 105 may additionally include a local microcontroller to monitor the performance of the system and reset the PIM to a known safe state in the event of loss of communication or system failure. PIM 105 may communicate with computer device 120 via a low speed RS232 serial link.

Figure 4:
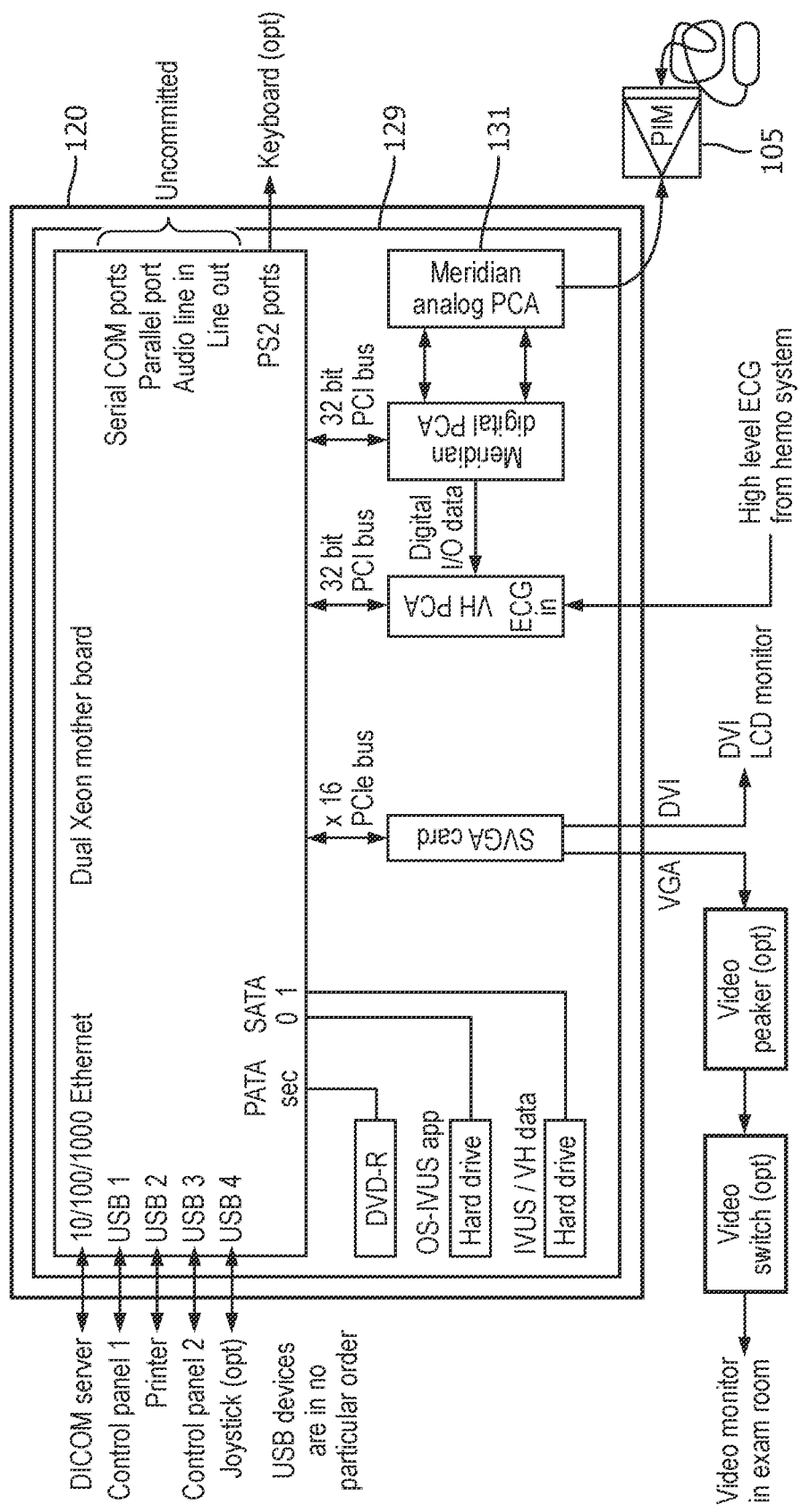
FIG. 4 describes components of computer device of certain embodiments.

FIG. 4 describes components of computer device 120 according to certain embodiments. Computer device 120 may include a motherboard 129 that includes an IVUS signal generation and processing system. FIG. 4 provides a high-level diagram and any box shown therein may be taken to represent a unit of hardware, a unit of functionality to be performed by one or more pieces of hardware, modules of software, or combination thereof. The signal generation and processing system may include an analog printed circuit assembly (PCA) 131, an digital PCA 133, one or more filter modules, and a VH board 135. Analog PCA 131 and digital PCA 133 are used to excite transducer 114 via catheter 112 and to receive and process the gray scale IVUS signals. The VH board 135 is used to capture and pre-process the IVUS RF signals and transfer them to the main VH processing algorithm as run by a computer processor system (e.g., dual Xeon processors). PIM 105 is directly connected to the analog PCA 131. A computer system that includes a computer, such as one like that depicted in FIG. 4, can be configured to perform the signal processing of the invention. Exemplary signal processing and systems therefore are discussed in U.S. Pat. Nos. 8,298,147; 8,187,191; 6,450,964; 5,485,845; U.S. Pub. 2012/0220874; U.S. Pub. 2012/0184853; and U.S. Pub. 2007/0232933, the contents of which are incorporated by reference herein in their entirety.

Figure 5:
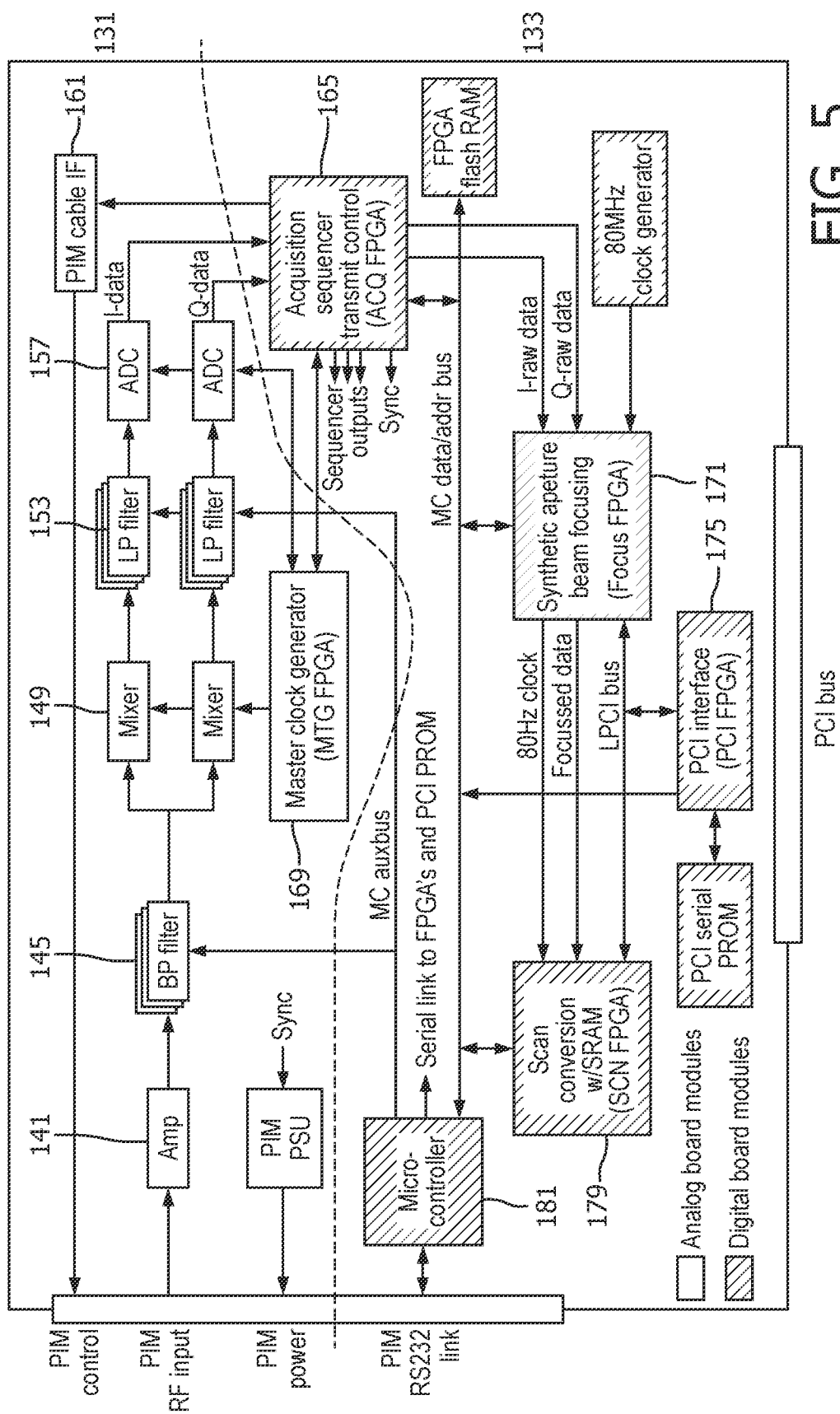
FIG. 5 provides a schematic of processing circuits.

FIG. 5 provides a schematic of analog PCA 131 and digital PCA 133 according to certain embodiments of the invention. Analog PCA 131 is shown to include amplifier 141, band pass filter 145, mixer 149, low pass filter 153, and analog-to-digital converter (ADC) 157. Here, the incoming signal is split just after bandpass filtering and prior to mixing by mixer 149. Mixer 149 performs the same function on each of two or more copies of the same signal. Then, low pass filter 153 performs the same low pass filtering function on each of the two or more copies of the same signal. Finally, ADC 157 converts each of the two or more copies of the same signal into a digital signal, and each of the two or more copies of the same digital signal is sent to the acquisition FPGA 165 for processing. Analog board 131 further includes an interface module 161 for PIM 105, as well as a clock device 169.

The invention provides systems and methods that incorporate the insight that unexpected benefits can be provided by splitting the signal and performing the counter-intuitive process of performing the same signal processing operations on each copy of the split signal. Established thinking suggests splitting a signal to perform different operations on each copy of the split signal. Here, since computer 120 splits the pathway and performs the same processing operations on each pathway, the system is readily adaptable for future changes that would require different processing operations. In one particular example, a signal is processed according to a parametric processing operation that is used to characterize the imaged tissue, such as in virtual histology. In some embodiment, virtual histology applications involve a processing step that makes use of a neural network comprising interconnecting artificial neurons, e.g., as supplied by a computer processing system. In virtual histology, a neural network can be taught to characterize tissue and to infer tissue characteristics from an incoming set of data. In some embodiments, to be effective, a tissue analyzing neural network should be trained on signals that are processed according to the same pathway as the subject signals upon which the neural network operates. Where the neural network is receiving a signal from, for example, an IVUS system that is also being use to provide an image (e.g., on a monitor), and change in the IVUS processing pathway would diminish the capabilities of the neural network. For example, if a physician using IVUS wanted to turn ringdown subtraction on and off, the different signals could produce sub-par results in the VH application. In some cases, a new insight in IVUS imaging may call for an upstream change in signal processing. For example, it may be desired to implement a new graphic equalization on IVUS signals using a mixer 149. If a single signal goes through mixer 149 and is split thereafter, then implementing the graphic equalization would require re-training the neural network—i.e., the existing neural network learning would no longer be useful. Where a system has been deployed with a split upstream of mixer 149, as depicted in FIG. 5, even though mixer 149 may perform the same function on both paths when the system is first installed, the system is readily adapted to the new graphic equalization function when implemented, without disrupting the neural network.

This adaptability becomes particularly useful when the subsequent changes involve inherently tunable processing parameters such as graphic equalization. One advantage of graphic equalization (or other parallelized processing such as multiband low pass filtering) is that it allows field-deployed fine tuning. If the signal were not split upstream of the tunable processor, then the other analysis modality (e.g., VH; high- versus low-frequency IVUS; blood flow characterization; simple data storage; others; or a combination thereof) would be compromised. While depicted in FIG. 5 as splitting the signal after bandpass filtering, one insight of the invention is that there can be value in splitting the signal at any point and subsequently performing the same processing step on the split. For example, in some embodiments, a signal is split within a processor such as a field programmable gate array and the two signal copies are also processed within that processor, with the processor performing the same operations on each signal path.

Digital PCA 133 is depicted as having an acquisition FPGA 165, as well as a focus FPGA 171, and a scan conversion FPGA 179. Focus FPGA 171 provides the synthetic aperture signal processing and scan conversion. In some embodiments, a single signal is sent into acquisition FPGA 165; split within FPGA 165; and processed in duplicate within FPGA 165. In some embodiments, a single signal is sent into acquisition FPGA 171; split within FPGA 171; and processed in duplicate within FPGA 171. In certain embodiments, two like signals are both focused (e.g., according to a synthetic aperture modality) within FPGA 171, having been split from a single incoming signal anywhere upstream from the focusing transistor hardware of FPGA 171. FPGA 179 provides the final scan conversion of the transducer vector data to Cartesian coordinates suitable for display via a standard computer graphics card on monitor 103. Digital board 133 further optionally includes a safety microcontroller 181, operable to shut down PIM 105 as a failsafe mechanism. Preferably, digital PCA 133 further includes a PCI interface chip 175. It will be appreciated that this provides but one exemplary illustrative embodiment and that one or skill in the art will recognize that variant and alternative arrangements may perform the functions described herein. Clock device 169 and acquisition FPGA 165 may operate in synchronization to control the transmission of acquisition sequences.

Figure 6:
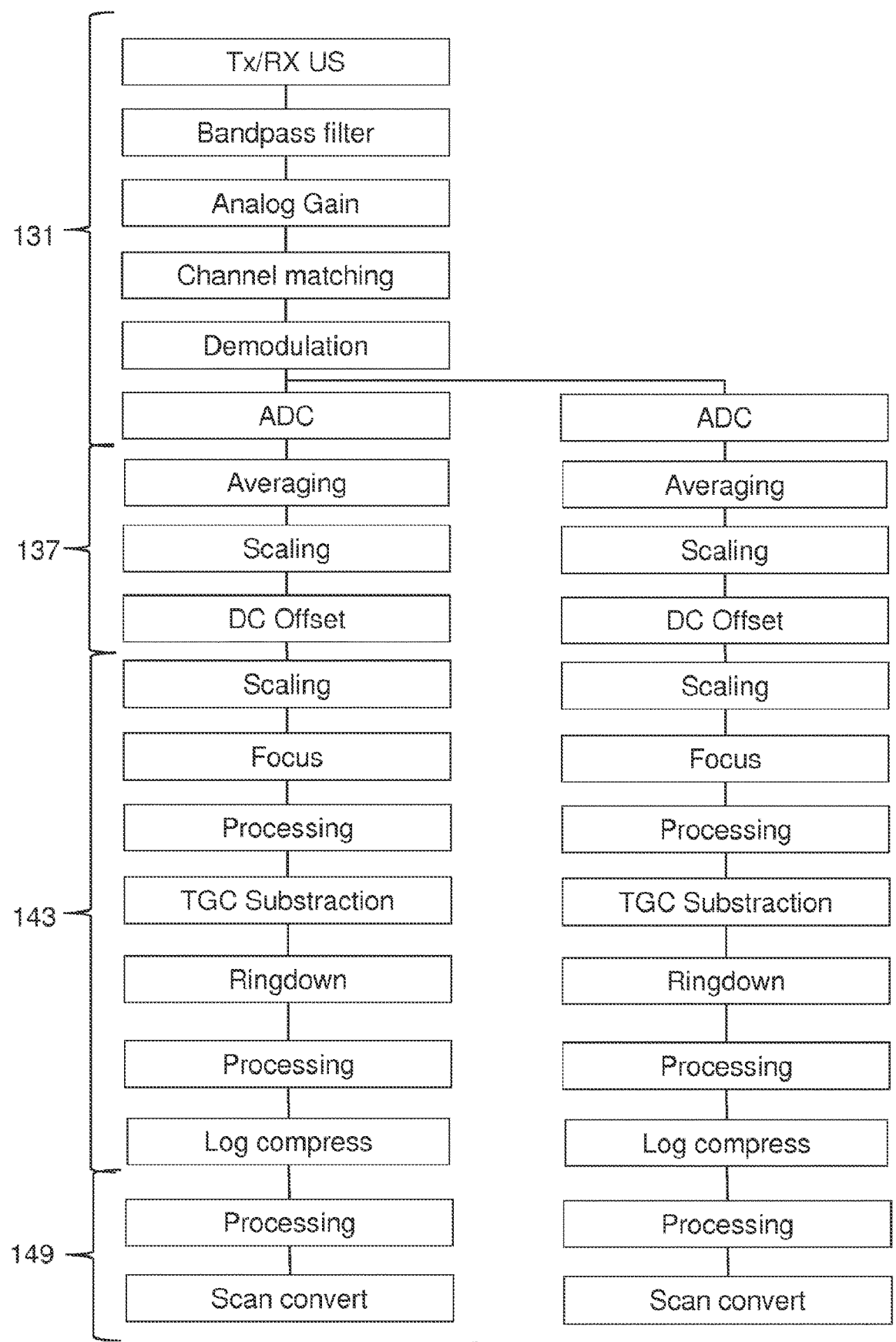
FIG. 6 is a diagram of ultrasound signal processing in two pathways for images

FIG. 6 provides a diagram of an embodiment of multipath processing of image signals. An ultrasound (US) transducer 114 receives (Rx) the signal that was transmitted (Tx). Further preprocessing operations 131 after the ultrasound (US) transmit (Tx) and receive (Rx), can include any desired bandpass filtering, analog gain, channel matching, demodulation, other steps, or a combination thereof. The analog signal is split into a first image signal and a second image signal and an analog-digital converter (ADC) performs a processing operation on the first image signal and the second image signal. Additional digital pre-processing operations 137 can include averaging, scaling, and DC offset correction. It will be appreciated by one skilled in the art that processing operation steps discussed herein can be performed in order other than shown here. Imaging processing operations 143 can then be performed and can include scaling, focus, processing, time gain compensation (TGC), ringdown subtraction, any additional processing, log conversion, other steps, or a combination thereof. Finally, an image can be prepared by image preparation operations 149 including, for example, any desired processing (e.g., contrast adjustment) and scan conversion.

Image processing operations can include any such operations known in the art or those discussed herein and need not be limited to, nor include all of, those listed in FIG. 6. In general, a bandpass filter is used to remove or attenuate certain (e.g., non-desired or non-intended) frequencies from the signal. Gain generally refers to adjusting a signal strength (e.g., with an amplifier) to a desired strength. Demodulation can include removing a carrier signal from a signal. Averaging can refer to average a series of A lines for improved signal-to-noise ratio (sometimes called accumulation). Scaling can refer to a linear transformation of the signal. DC offset correction can include removing or adding a constant amplitude to a signal to produce an AC signal with an average amplitude near or at zero. Focusing can include using incoming sounds from adjacent Tx events to improve an A line. Time gain compensation (TGC) refers to adjusting the signal to compensate for a non-uniform signal strength based on attenuation in the IVUS backscatter strength relating to an amount of time that the sound signal was passing through tissue. Ringdown refers to transient sounds from vibration of transducer that can be removed in ringdown subtraction. Scan conversion can include transforming a 3D data set in preparation for a 2D display and can proceed by a fast Fourier transformation. By scan conversion, a B mode image is prepared from a set of A lines. Signal processing steps are discussed in more detail in U.S. Pat. Nos. 8,289,284; 8,187,191; 6,254,543; 6,200,268; U.S. Pub. 2012/0220874; U.S. Pub. 2011/0087104; and U.S. Pub. 2010/0234736, the contents of which are incorporated by reference herein in their entirety.

Figure 7:
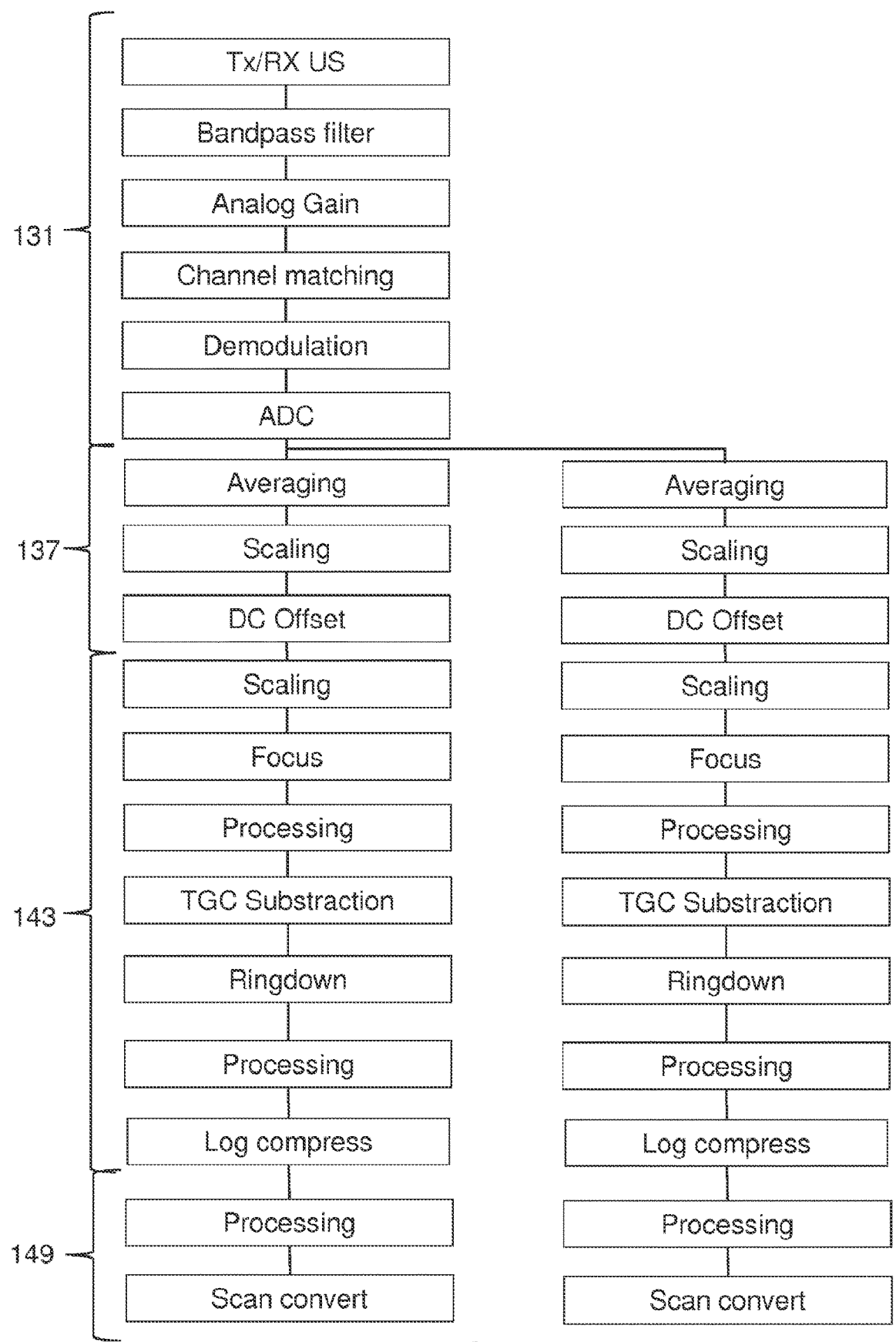
FIG. 7 shows a multipath signal processing scheme for ultrasound images.

FIG. 7 shows an alternative embodiment in which a signal is split just after digitization at the end of preprocessing operations 131. Here, any of the additional digital pre-processing operations 137, imaging processing operations 143, image preparation operations 149, or a combination thereof are performed in duplicate on the first image signal and the second image signal, which contain substantially the same information as one another through at least one of the shared processing steps.

Figure 8:
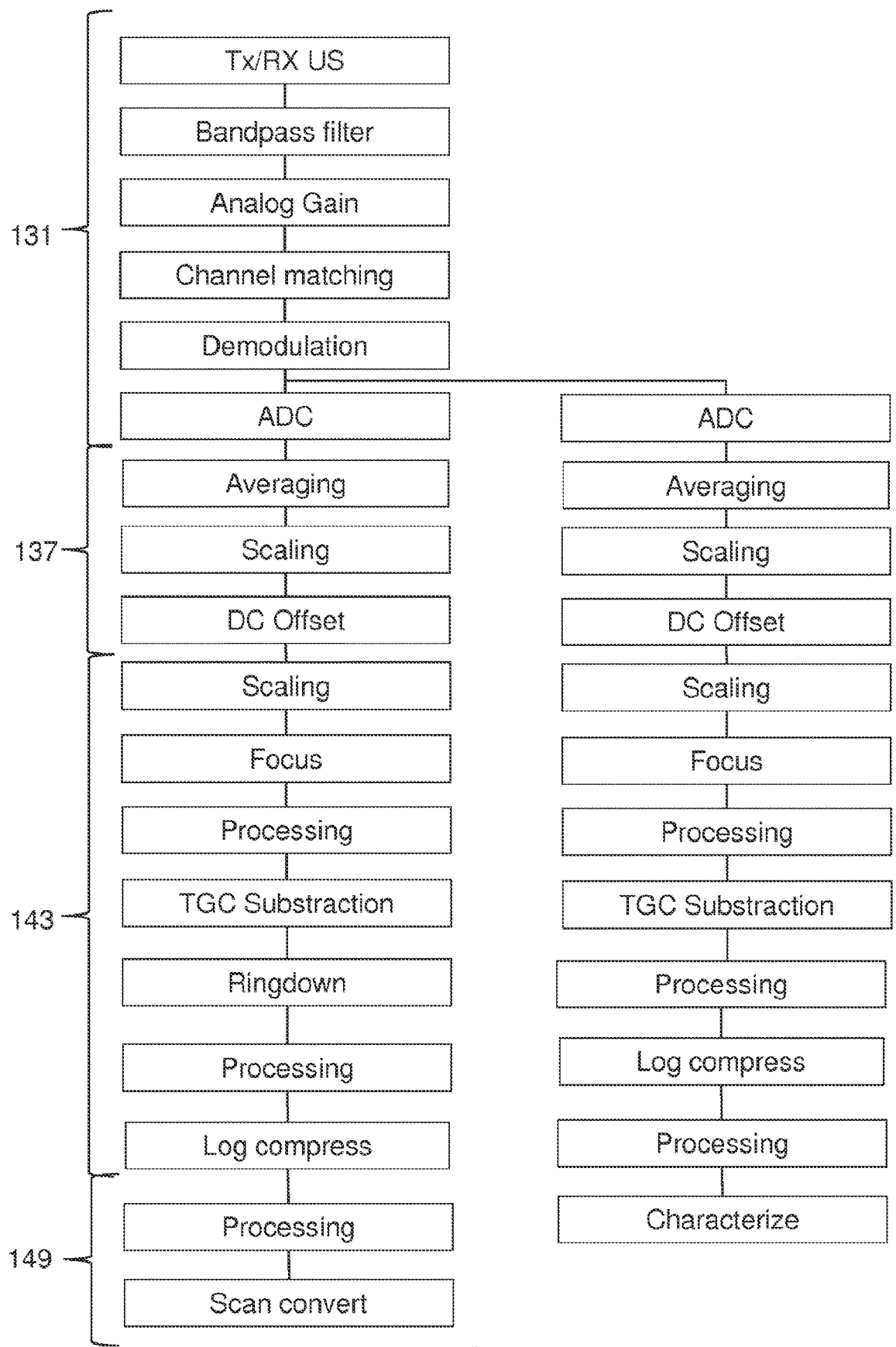
FIG. 8 shows a signal processing scheme for an image and for a parametric analysis.

FIG. 8 depicts an embodiment in which a signal is received and preprocessing operations 131 are performed, after which the signal is split, and the first and second copies of the split signal are digitized. Additional digital pre-processing operations 147 may be performed on each of the first and second signal. Further, the first signal undergoes all of the signal processing discussed above with respect to FIG. 6. Here, the second signal undergoes processing in preparation for a parametric analysis such as a VH tissue characterization. Any of imaging processing operations 143 may be performed on the second (VH) signal path, however any or most of them may not. For example, ringdown subtraction is not performed on the VH path. Here, final preparation operations 149 for VH characterization can include a processing step that involves analysis by a neural network, after which the image can be used to characterize the tissue.

Figure 9:
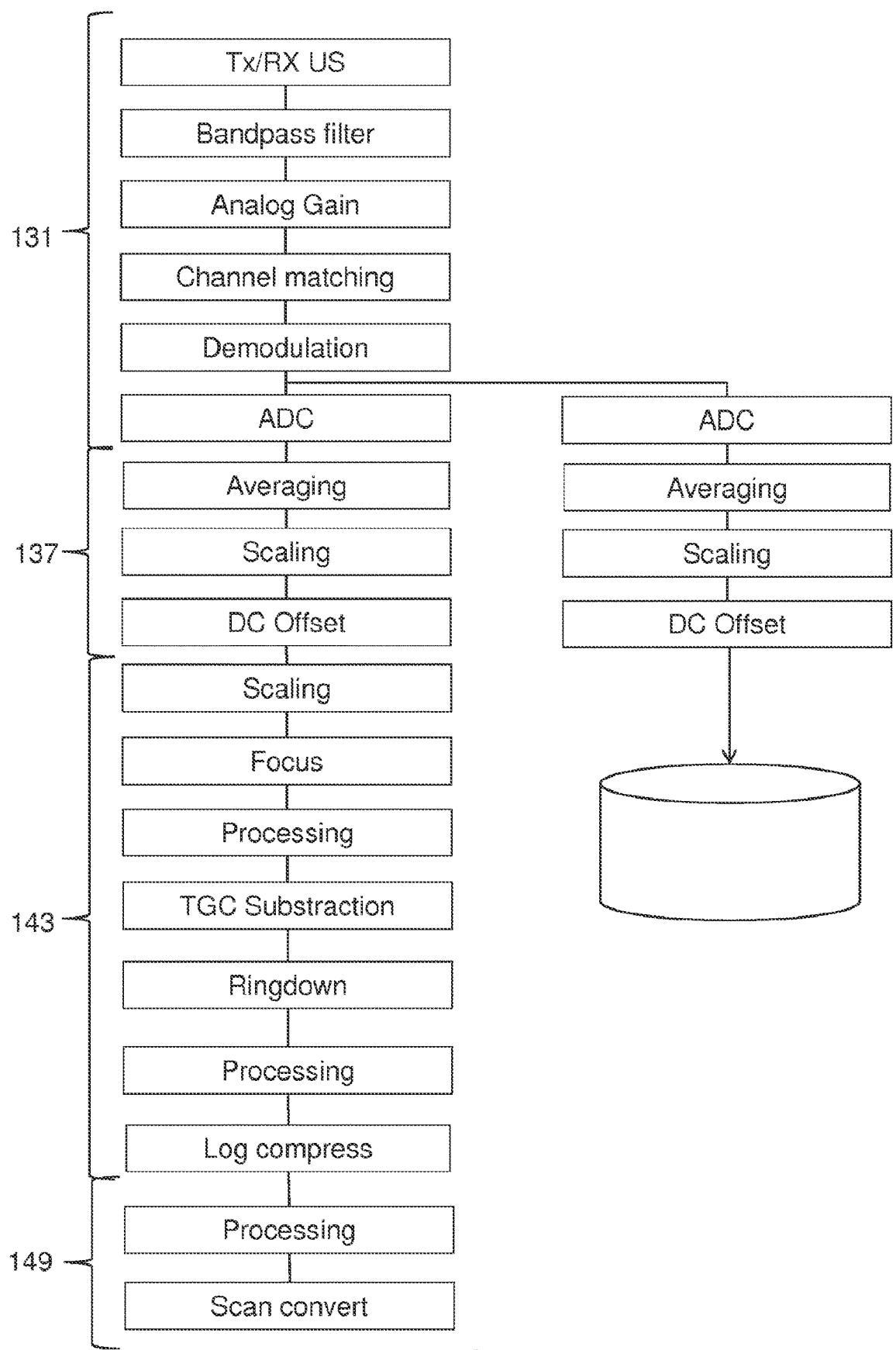
FIG. 9 shows a multipath signal processing scheme for flexibility.

FIG. 9 depicts a multipath signal processing scheme in which a second signal path is routed to storage for later flexibility. Here, even where the second signal path does not directly contribute to producing an analytical result simultaneously with the scan converted image provided by the first signal path, the presence of a second signal path shunt in system 120 allows a later analytical modality to be added to system 120. Any amount of additional digital pre-processing operations 137 may be performed on the first and second signal path after it is split. Then the second signal path can be routed to storage and stored. Storage of the second set of signals can have benefit because, even if processing of the first signal path changes over time, the accumulated signals stored from the second path have all been processed according to the same steps. A VH algorithm could be introduced and the neural network could be trained on the stored data. A subsequent problem in the first path could be diagnosed by calibrating first path images against path two data to establish, at what point in time, some change had occurred.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An intravascular ultrasound (IVUS) imaging system, the system comprising:
   an elongated catheter configured to be positioned within a blood vessel of a patient, wherein the elongated catheter comprises a proximal portion, a distal portion, and an ultrasound transducer at the distal portion; and
   a processing circuit configured for communication with the elongated catheter, wherein the processing circuit is operable to:
   activate generation of an IVUS image with a first visual appearance;
   activate generation of the IVUS image with a second visual appearance;
   receive a single analog image signal from the ultrasound transducer;
   split the single analog image signal into a first analog image signal and a second analog image signal, the first analog image signal comprising a copy of the second analog image signal;
   digitize the first analog image signal to a first digital image signal using a first analog-to-digital converter along a first signal path and the second analog image signal to a second digital image signal using a second analog-to-digital converter along a second signal path;
   perform a first set of processing operations on the first digital image signal along the first signal path, wherein the first set of processing operations includes a first visual appearance operation inconsistent with the generation of the IVUS image with the second visual appearance;
   perform a second set of processing operations on the second digital image signal along the second signal path, wherein the second set of processing operations includes a second visual appearance operation different from the first visual appearance operation;
   generate the IVUS image with the first visual appearance based on the first digital image signal and the IVUS image with the second visual appearance based on the second digital image signal; and
   output the IVUS image with the first visual appearance and the IVUS image with the second visual appearance to a display in communication with the processing circuit.

2. The IVUS imaging system of claim 1, wherein the first set of processing operations comprises generating qualitative or quantitative blood flow data, and wherein the IVUS image with the first visual appearance includes visual representations of the qualitative or quantitative blood flow data.

3. The IVUS imaging system of claim 1, wherein the first set of processing operations comprises automatically generating a boundary in the IVUS image with the first visual appearance, and wherein the IVUS image with the first visual appearance includes the boundary.

4. The IVUS imaging system of claim 1, wherein the first set of processing operations includes graphic equalization of the first digital image signal using a mixer.

5. The IVUS imaging system of claim 1, wherein the second visual appearance operation includes tissue characterization based on at least one of parametric analysis, spectral analysis, or a neural network.

6. The IVUS imaging system of claim 5, wherein the IVUS image with the second visual appearance comprises a virtual histology image.

7. The IVUS imaging system of claim 6, wherein the tissue characterization is configured to identify at least one of plaque, dead tissue, or healthy tissue.

8. The IVUS imaging system of claim 1, wherein the first set of processing operations includes processing by a hardware amplifier or filter.

9. The IVUS imaging system of claim 1, wherein the first set of processing operations includes at least one of a band pass filter, a low-pass filter, a multi-band low pass filter, or a gain.

10. The IVUS imaging system of claim 1, wherein the second set of processing operations includes at least one of a band pass filter or a gain.

11. The IVUS imaging system of claim 1, wherein the processing circuit is further operable to:
receive a first user input activating the generation of the IVUS image with the first visual appearance;
receive a second user input activating the generation of the IVUS image with the second visual appearance;
perform the first set of processing operations based on the first user input; and
perform the second set of processing operations based on the second user input.

12. The IVUS imaging system of claim 1, wherein the second set of processing operations omits the first visual appearance operation.

13. An intravascular ultrasound imaging system, the system comprising:
an elongated catheter comprising an ultrasound transducer at a distal portion of the elongated catheter, wherein the elongated catheter is coupled to a processing system at a proximal portion of the elongated catheter, and wherein the processing system is operable to:
receive a single analog image signal from the ultrasound transducer;
split the single analog image signal into a first analog image signal and a second analog image signal, the first analog image signal comprising a copy of the second analog image signal;
digitize the first analog image signal to a first digital image signal using a first analog-to-digital converter along a first signal path and the second analog image signal to a second digital image signal using a second analog-to-digital converter along a second signal path;
perform a first processing operation on the first digital image signal along the first signal path and perform the same first processing operation on the second digital image signal along the second signal path;
receive user input to re-configure the first signal path to perform a second processing operation on only the first digital image signal to subtract ringdown artifacts;
derive a first type of image from the first digital image signal following a re-configuration of the first signal path; and
derive a second type of image from the second digital image signal including the ringdown artifacts.

14. The system of claim 13, wherein the processing system comprises a time gain compensation (TGC) amplifier operable to produce a TGC amplified first signal and a TGC amplified second signal.

15. The system of claim 13,
wherein the processing system comprises a field-programmable gate array configured to perform the first processing operation to produce a processed first image signal and a processed second image signal, and
wherein the processed first image signal is substantially the same as the processed second image signal.

16. The system of claim 13, wherein the processing system comprises one selected from the list consisting of a field-programmable gate array, an application-specific integrated processor, a time-gain compensation amplifier, a low-band pass filter, and a massively parallel processor array.

17. The system of claim 13, wherein the first type of image comprises a B-mode grayscale image and the second type of image comprises a virtual histology image.

18. The system of claim 17, wherein the processing system is operable to derive the second type of image by performing tissue characterization on the second digital image signal including the ringdown artifacts.

19. The system of claim 13, wherein the processing system includes a tunable processor configured to receive the user input to re-configure the first signal path.

20. The system of claim 19, wherein the tunable processor comprises a graphics equalizer.

21. The system of claim 13, further comprising a control panel including at least one switch configured to turn off at least one processing operation along only the first signal path without affecting processing operations along the second signal path.

22. The system of claim 21, further comprising a neural network associated with the second signal path.

* * * * *